(12) United States Patent
Hansen et al.

(10) Patent No.: US 8,449,773 B2
(45) Date of Patent: May 28, 2013

(54) METHOD FOR PRETREATMENT OF CELLULOSIC AND LIGNOCELLULOSIC MATERIALS FOR CONVERSION INTO BIOENERGY

(75) Inventors: Jaron C. Hansen, Springville, UT (US); Lee D. Hansen, Saratoga Springs, UT (US)

(73) Assignee: Brigham Young University, BYU, Provo, UT (US)

( * ) Notice: Subject to any disclaimer, the term of this patent is extended or adjusted under 35 U.S.C. 154(b) by 129 days.

(21) Appl. No.: 12/863,439

(22) PCT Filed: Jul. 6, 2010

(86) PCT No.: PCT/US2010/041095
§ 371 (c)(1),
(2), (4) Date: Jul. 17, 2010

(87) PCT Pub. No.: WO2011/005782
PCT Pub. Date: Jan. 13, 2011

(65) Prior Publication Data
US 2011/0117619 A1 May 19, 2011

Related U.S. Application Data

(60) Provisional application No. 61/270,235, filed on Jul. 6, 2009.

(51) Int. Cl.
*C02F 1/72* (2006.01)
*C02F 11/04* (2006.01)
*A61K 38/00* (2006.01)

(52) U.S. Cl.
USPC ........... 210/627; 210/621; 210/622; 210/623; 210/624; 210/631; 435/158; 435/162; 435/192

(58) Field of Classification Search
None
See application file for complete search history.

(56) References Cited

U.S. PATENT DOCUMENTS

| | | | |
|---|---|---|---|
| 4,008,136 A | 2/1977 | Williams | |
| 4,216,054 A | 8/1980 | Bentvelzen | |
| 4,314,854 A | 2/1982 | Takagi | |
| 4,806,475 A | 2/1989 | Gould | |
| 4,863,608 A | 9/1989 | Kawai | |
| 5,015,384 A * | 5/1991 | Burke | 210/603 |
| 5,023,097 A | 6/1991 | Tyson | |
| 5,221,357 A | 6/1993 | Brink | |
| 5,258,124 A | 11/1993 | Bolton | |
| 5,658,429 A | 8/1997 | Andersson | |
| 5,762,808 A | 6/1998 | Peyton | |
| 5,865,898 A | 2/1999 | Holtzapple | |
| 6,117,324 A | 9/2000 | Greene | |
| 6,342,378 B1 | 1/2002 | Zhang | |
| 6,500,333 B1 | 12/2002 | Greene | |
| 6,546,740 B1 | 4/2003 | DesMarteau | |
| 6,548,438 B2 | 4/2003 | Brosnan | |
| 6,555,350 B2 | 4/2003 | Ahring | |
| 6,835,560 B2 | 12/2004 | Greene | |
| 6,893,565 B2 | 5/2005 | Greene | |
| 7,189,306 B2 | 3/2007 | Gervais | |
| 7,297,274 B2 | 11/2007 | Wilkie | |
| 7,452,467 B2 | 11/2008 | Hansen | |
| 7,488,425 B2 | 2/2009 | Fuchigami | |
| 7,498,163 B2 | 3/2009 | Greene | |
| 2002/0192774 A1 | 12/2002 | Ahring et al. | |
| 2003/0077770 A1 | 4/2003 | Greene | |
| 2005/0141966 A1 | 6/2005 | Greene | |
| 2006/0207734 A1 | 9/2006 | Day | |
| 2007/0259412 A1 | 11/2007 | Belanger | |
| 2008/0026431 A1 | 1/2008 | Saito | |
| 2009/0004692 A1 | 1/2009 | Vande Berg et al. | |
| 2009/0178671 A1 * | 7/2009 | Ahring et al. | 127/37 |
| 2011/0155559 A1 * | 6/2011 | Medoff | 204/157.63 |

FOREIGN PATENT DOCUMENTS

| | | |
|---|---|---|
| AT | 411971 T | 11/2008 |
| AU | 2122100 A | 8/2001 |
| AU | 3362101 A | 8/2001 |
| AU | 200133621 A1 | 8/2001 |
| BR | 0017078 A | 11/2002 |
| CA | 2399400 A1 | 8/2001 |
| CA | 2400336 A1 | 8/2001 |
| CA | 2400336 C | 4/2010 |
| CN | 1437564 A | 8/2003 |
| CN | 1443141 A | 9/2003 |

(Continued)

OTHER PUBLICATIONS

Fermor T.R. (1993) Applied aspects of composting and bioconversion of lignocellulosic materials: An overview, Internat. Biodetect. Biodegrad., vol. 31, issue 2, pp. 87-106.*
Valo et al. (2004) Thermal, chemical and thermo-chemical pre-treatment of waste activated sludge for anaerobic digestion, J. Chem. Technol. Biotech., vol. 79, pp. 1197-1203.*
Muhammad et al. (2008) Decolorization and Removal of COD and BOD From Raw and Biotreated Textile Dye Bath Effluent Through Advanced Oxidation Processes (AOPS), Braz. J. Chem. Eng., vol. 25, No. 3, pp. 453-459.*
Taherzadeh et al. (2008) Pretreatment of Lignocellulosic Wastes to Improve Ethanol and Biogas Production: A Review, Int. J. Mol. Sci., vol. 9, pp. 1621-1651.*

(Continued)

*Primary Examiner* — Anand Desai
*Assistant Examiner* — Samuel Liu
(74) *Attorney, Agent, or Firm* — Jacob C. Ong, Ongs Law Firm, PLLC

(57) ABSTRACT

A process for converting organic waste materials into usable products and products thereof is disclosed. According to the process, organic waste materials are contacted with an oxidant to form a product and then an amount of the oxidant is removed from the product to form a reactor-ready feedstock. The oxidant is removed by various means, including washing, photolysis, catalytic means, oxidation of the oxidant, reduction of the oxidant, and heat. The reactor-ready feedstock may then be introduced into a reactor, such as a digester or incubator, and the reactor-ready feedstock is converted by microorganisms into biofuel or other products.

14 Claims, 6 Drawing Sheets

FOREIGN PATENT DOCUMENTS

| | | |
|---|---|---|
| CN | 1190373 | 2/2005 |
| CN | 1190373 C | 2/2005 |
| CN | 1243669 C | 3/2006 |
| DE | 60032179 | 1/2007 |
| DE | 60032179 T2 | 9/2007 |
| DE | 60136267 | 12/2008 |
| DK | 1259466 T3 | 1/2009 |
| EP | 1259466 A1 | 11/2002 |
| EP | 1263686 A1 | 12/2002 |
| EP | 1444058 A1 | 8/2004 |
| EP | 1263686 B1 | 11/2006 |
| EP | 1444058 A4 | 1/2007 |
| EP | 1259466 B1 | 10/2008 |
| ES | 2275490 T3 | 6/2007 |
| ES | 2315272 T3 | 4/2009 |
| JP | 2003521258 A | 7/2003 |
| JP | 2003521258 T | 7/2003 |
| JP | 04285933 B2 | 4/2009 |
| JP | 4285933 B2 | 6/2009 |
| KR | 100808736 B1 | 2/2008 |
| MX | PA02007361 A | 9/2004 |
| WO | WO0156938 A1 | 8/2001 |
| WO | WO0160752 A1 | 8/2001 |
| WO | WO03033181 A1 | 4/2003 |
| WO | WO2006032282 A1 | 3/2006 |
| WO | WO2008137639 A1 | 11/2008 |

OTHER PUBLICATIONS

Lewis, "Effects of Alkaline Hydrogen Peroxide Treatment on in Vitro Degradation of Cellulosic Substrates by Mixed Ruminal Microorganisms and Bacteroides succinogenes S85," Applied and Environmental Microbiology, May 1988, p. 1163-1169, vol. 54, No. 5, American Society for Microbiology.

Vaghjiani, "Photodissociation of H20 2 and CH300H at 248 nm and 298 K: Quantum yields for OH, 0(3P) and H(2S)," J. Chem Phys , 1990, p. 996-1003, vol. 92, Issue 2.

Turnipseed, "Photodissociation of HN03 at 193, 222, and 248 nm: Products and quantum yields," J. Chem. Phys., 1992, p. 5887-5895, vol. 96, Issue 8.

Stalin, "Performance Evaluation of Partial Mixing Anaerobic Digester," ARPN Journal of Engineering and Applied Sciences, Jun. 2007, p. 1-6, vol. 2, No. 3, Asian Research Publishing Network.

\* cited by examiner

| Heat production (pretreated/untreated cellulose) | Volume of 30% hydrogen peroxide used/g of cellulose |
|---|---|
| 3.73 | 250 µl |
| 5.56 | 300 µl |
| 4.82 | 650 µl |
| 7.61 | 1000 µl |

Figure 3

METHOD FOR PRETREATMENT OF CELLULOSIC AND LIGNOCELLULOSIC MATERIALS FOR CONVERSION INTO BIOENERGY

CROSS REFERENCE TO RELATED APPLICATION

This application claims the benefit of U.S. Provisional Patent Application No. 61/270,235, filed 6 Jul. 2009, which is incorporated in its entirety by this reference.

TECHNICAL FIELD OF THE INVENTION

The present invention relates generally to methods and processes for converting organic materials and organic waste materials into a form that is readily converted into bioenergy.

BACKGROUND OF THE INVENTION

The present invention relates generally to methods and processes for converting organic materials and organic waste materials into a form that is readily converted into bioenergy. In recent years, efforts have been devoted to developing energy sources that are alternatives to traditional fossil fuel sources. Some noted problems with fossil fuel are: the potential effects on global warming, the cost of obtaining fossil fuel, and the nonrenewable nature of fossil fuels.

Plants use photosynthesis to store energy from the sun in biomass. A demand exists for cost-effective methods for converting the energy stored in biomass into a form of energy that is readily used by humans. Cellulosic and lignocellulosic biomass is particularly well-suited for energy applications because of its large-scale availability, low cost, and environmentally benign production. For example, conversion of cellulosic and lignocellulosic material into bioenergy may be advantageous, given the rapid growth of algae, switchgrass, other fast-growing grasses, and short rotation woody crops such as shrub willow (*Salix* spp.) and poplar (*Populus* spp.) Other examples of lignocellulosic material include, but are not limited to, wood chips, leaves, corn stalks, straw, grass, rice straw, municipal cellulosic waste, animal manure, and human sewage.

Lignocellulose makes up much of the structural matter of plants. Cellulose, hemicellulose, and lignin are the principle components of lignocellulose. Most notably, attempts have been made to convert lignocellulosic material into bioenergy; however, the structure of plant-derived materials presents inherent problems. In a typical lignocellulosic biomass process, raw material feedstock, which is primarily composed of cellulose, is ground up and then pretreated (usually with acid or alkali) to break down the cellulose and separate the three main components of wood (cellulose, hemi-cellulose and lignin). These components are then acted upon by enzymes to form a reactor-ready feedstock, which is a fermentable mixture of glucose and xylose (the basic component of hemicellulose). This mixture is then fermented and distilled to create ethanol. However, pretreatment by alkali or acid is accompanied by problems in recovery or disposal of waste alkali or waste acid.

Methods known in the art for pretreating raw material feedstock for use in a reactor, such as an anaerobic digester or a partially-anaerobic digester, include enzymatic treatment; however, enzymatic treatment is relatively slow and costly. Nonetheless, Iogen, Broin, Abengoa and other companies are building plants to process organic material into ethanol. Companies like Diversa, Novozymes, and Dyadic are researching enzymes which can convert cellulose into sugars that can then be fermented to produce ethanol. Andigen uses anaerobic digestion to partially convert biomass into methane; however, the economic viability of conversion of biomass into methane has remained questionable.

An alternative to ethanol production would be to produce methane and/or hydrogen from lignocellulosic material. Currently, anaerobic and partially-anaerobic digesters are useful for converting raw material feedstock into methane and/or hydrogen; however, the yield of methane and/or hydrogen gas from current methods is low and inefficient because most organisms struggle to break down lignin, lignocelluloses, and cellulose, which all have inherent structural stability.

Strong oxidizing agents, such as ozone, have been used to pretreat organic materials. These processes can be used in conjunction with strong acids and bases. However, the use of these methods is relatively costly.

Hence, the need still exists for a simple, cost-effective, and efficient method that could be used by the individual consumer and also be scaled-up for use at waste treatment plants, landfills, and other operations.

The literature is replete with examples of pretreatment protocols; thus, the following pieces of literature are incorporated in by reference. The following U.S. Patents are incorporated by reference: U.S. Pat. Nos. 4,216,054; 4,314,854 4,806,475; 5,023,097; 5,221,357; 5,658,429; 5,865,898; 6,117,324; 6,342,378; 6,500,333; 6,546,740; 6,548,438; 6,555,350; 6,835,560;6,893,565; 7,189,306; 7,297,274; and 7,498,163. U.S. Pat. No. 7,452,467 discloses an example of an anaerobic digester, i.e. the induced blanket reactor, and is incorporated by reference. An induced blanket reactor is one example of a reactor that can be used to convert pretreated organic material into biofuel.

The following U.S. patent applications are incorporated by reference: 2006/0207734; 2007/0259412; 2008/0026431. The following WIPO patent applications are incorporated by reference: WO 2006/032282 and WO 2008/137639. The WO 2008/137639 application ("the '639 application") and U.S. Pat. No. 7,498,163 ("the '163 patent) both claim methods that include the addition of hydrogen peroxide; however, both claimed processes are non-enabling and would not allow one skilled in the art to practice the invention without undue experimentation. In addition, the concentration of hydrogen peroxide that is used is important. Without the specific parameters that are disclosed herein, undue experimentation would be required before one skilled in the art could determine the optimal concentration of peroxide that is claimed in the present invention.

Removal of the peroxide is an important step. If the peroxide is not removed after pretreatment of the raw material feedstock, use of the reactor-ready feedstock in a reactor, such as an anaerobic digester or a partial-anaerobic digester, will cause extensive foaming because bacterial enzymes will interact with the peroxide to release oxygen ($O_2$); additionally it is believed that peroxides react with organic material to form organic peroxides. These organic peroxides tend to be difficult to destroy and also have the effect of causing excessive foaming. Additionally, if the peroxide is not removed from the reactor-ready feedstock, then the reactor will be contaminated with peroxide which effectively sterilizes the reactor by killing some or all of the bacteria in the reactor.

Washing the reaction sample is one method known in the art to decrease the amount of peroxide that is present in a reaction sample. Washing away the peroxide from a reaction sample usually increases the cost, however, and removes soluble material that is desirable in the feedstock. Lewis et al. discloses experiments where alkaline hydrogen peroxide was used to treat straw. "Effects of Alkaline Hydrogen Peroxide Treatment on In Vitro Degradation of Cellulosic Substrates by Mixed Ruminal Microorganisms and *Bacteroides succinogenes* S85, Sherry M. Lewis et al. (1988). Some of the treated samples were unwashed, and some were washed thoroughly to remove residual chemicals and then used in fermentation with mixed ruminal microorganisms. Id.

Photolysis is another means for removing peroxide. Some U.S. patents that contain references to photolysis include: U.S. Pat. Nos. 7,488,425 (Method for photolyzing organic matter and method for treating wastewater); 5,762,808 (Destruction of electron affinic contaminants during water treatment using free radical processes); 5,258,124 (Treatment of contaminated waste waters and groundwaters with photolytically generated hydrated electrons); 4,863,608 (Photocatalytic treatment of water for the preparation of ultra pure water); and, 4,008,136 (Process for the treatment of waste water by heterogeneous photosensitized oxidation).

The photolysis of $H_2O_2$ by light with wavelengths that are greater than 189 nm in length and less than 249 nm in lengths has been shown to split hydrogen peroxide to produce two hydroxyl radicals; these hydroxyl radicals are reactive oxidizing agents. See Vaghjiani, G. L. and A. R. Ravishankara, 1990, *J. Chem. Phys.*, 92, 996 and Vaghjiani, G. L. A. A., Turnipseed, R. F. Warren, and A. R. Ravishankara, 1192, *J. Chem. Phys.*, 96, 5878.

SUMMARY OF THE INVENTION

The following description of the invention should make it clear to the reader that using the invention will allow one skilled in the art to minimize the cost-benefit ratio of converting organic material to biofuel, converting organic material to products that can be used to make biofuel, or reducing the volume and mass of waste products. For example, the following invention could be used to convert corn stalks into biofuel. Recent developments associated with the production of low-cost peroxide make the invention and embodiments of the invention more cost-effective then existing technologies for large-scale conversion of organic material into storable bioenergy.

The present invention provides improved processes and methods for pretreating organic material, also known as raw material feedstock, for use in a reactor, such as an anaerobic reactor or partial-anaerobic reactor. More particularly, the invention relates to the pretreatment of cellulosic, lignocellulosic, or cellulosic and lignocellulosic material for use in an anaerobic or partially-anaerobic reactor. Preferably, a peroxide or other oxidizing agent is used to partially oxidize the cellulosic or lignocellulosic material, the oxidizing agent is removed, and the remaining reactor-ready feedstock product can be incubated in a reactor, such as an anaerobic reactor or a partially-anaerobic reactor, to produce bioenergy, products that can be used to form bioenergy, soil amendments, or waste materials that are reduced in mass and volume.

One aspect of the present invention is a process for pretreating a slurry of organic material, comprising:

a) combining organic material with a dilute, aqueous peroxide solution, wherein a first product is formed; and, b) removing a portion of the peroxide contained in the first product, wherein a pretreated-feedstock is formed.

One aspect of the invention is that the concentration of the peroxide in the dilute, aqueous peroxide solution is sufficiently high so that the peroxide can sufficiently partially oxidize the raw material feedstock, and the amount of active peroxide in the reactor-ready feedstock is sufficiently low so that the reactor-ready feedstock can be used in a reactor without creating extensive foam or altering the bacterial culture in the reactor. (Extensive foaming is any amount of foam that: materially affects the reaction of the reactor-ready feedstock in the reactor or sterilizes the reactor so that further reactions in the reactor are materially affected.) Thus, removing the peroxide, or a significant portion of the peroxide, from the mixture comprising partially oxidized feedstock and peroxide, is an important aspect of the invention; otherwise, the inventors have found that incubating the pretreated product in a reactor will generate an extensive amount of foam. (Removal of the peroxide can be accomplished by physically removing the peroxide or by chemical-inactivation of the peroxide. Heating, even boiling for an extended time, does not destroy hydrogen peroxide after mixing with cellulose.) One skilled in the art would likely not recognize the difficulty of removing or destroying the peroxide in the pretreated product unless one had actually conducted the experiment. Extensive foaming from peroxide decomposition is not desirable since extensive foam interferes with reactor operation and may interfere with the production and collection of methane or other products of the reaction carried out in the reactor.

In step a) of the process above, a first product is formed. The first product can also be termed the mixture comprising partially oxidized feedstock and peroxide. Non-limiting examples of the first product include a suspension of cellulosic material, a suspension of lignocellulosic material, a suspension of cellulosic and lignocellulosic material, a solution of cellulosic material, a solution of lignocellulosic material, or a solution of cellulosic and lignocellulosic material.

Washing the first product with a washing agent, such as water, is one possible method for removing the peroxide from the first product. Washing the first product could consist of mixing, contacting, or combining the first product with a washing agent followed by decanting or filtering the washing agent to reduce the concentration of peroxide or oxidant that is now in the washing agent, and retaining the solid which will eventually be converted to a biofuel, a product that can be used to make biofuel, or waste products. Reducing the concentration of peroxide or oxidant means to decrease the concentration of the peroxide or oxidants to such a level that the remaining peroxide or oxidant does not excessively foam or sterilize the reactor.

The washing agent that is used to wash the first product can be selected from the group comprising water, distilled water, deionized-distilled water, polar substances, catalysts, oxidizing agents, reducing agents, and combinations thereof. An example of a "combination thereof" would be a solution consisting of water and an oxidizing or reducing agent.

One aspect of this invention is to form a first product by contacting or combining the organic materials with sufficient peroxide to react in an approximately 1:1 molar ratio with the cellulose monomer that is estimated or determined to be in the organic material used to form the first product.

Methods for removing the peroxide include physically-removing the peroxide by washing, decanting, or filtering, chemically-inactivating the peroxide with catalysts, oxidizing agents, or reducing agents, photolyzing the first product, irradiating the first product, and combinations thereof.

There are many possible embodiments of the invention. Some embodiments of the invention consist of using one or more of the following oxidants: oxygen, hydrogen peroxide, peroxides, sodium percarbonate, sodium peroxycarbonate, sodium peroxide, calcium peroxide, organic peroxides, barium peroxide, superoxides, and any compound capable of producing a peroxide in a solution or suspension.

One embodiment of the invention contemplates processing the pretreated-feedstock in a reactor. Some non-limiting examples of a reactor include anaerobic reactors and partially-anaerobic reactors. Anaerobic bacteria, archaea, yeast, fungi, and other organisms may be present in the reactor; these organisms then digest the pretreated product and produce biofuel, compounds that can then be used in further reactions to make biofuel, or waste products—such as carbon dioxide.

The step of removing the peroxide or oxidant could be repeated for one or more times; for example; first, the mixture containing partially oxidized feedstock material could be washed and rinsed with water; second, the water could be decanted and the resulting product could then be washed again with a second amount of water; and third, the second amount of water could then be decanted. The washing and rinsing could be repeated one or more times until the first product was substantially free of peroxide.

As mentioned above, numerous methods exist to remove the peroxide from the first product which is contemplated by the invention. For example, the first product could be photolyzed with ultraviolet light, that is, the first product could be exposed to light with wavelengths in the range of 190 nm to 350 nm in length. Light with wavelengths in the range of 190 nm to 350 nm in length will deactivate peroxides by breaking down the oxygen to oxygen bonds, that is the O—O bonds, which exist in peroxides. Certain wavelengths of light, such as 190 nm to 350 nm, are not absorbed by water and could be used to photolyze the peroxide contained in the first product. This technique of decomposing peroxide is a relatively simple and cost-efficient method for removing excess peroxides from the first product, that is, the product which is formed after the slurry of organic material has been combined with the dilute, aqueous peroxide solution. In one embodiment of the invention, the product of the peroxide-organic material reaction is pumped into a transparent tube and is exposed to a ring of light while it is inside the tube or the product may be passed around a UV light source.

Other embodiments of the invention include methods where the dilute, aqueous peroxide is heated before it is added to the raw material feedstock. Optionally, the raw material feedstock is first heated and then the dilute, aqueous peroxide is added to the raw material feedstock. Alternatively, a mixture of the first product and dilute, aqueous peroxide solution could be heated after the dilute, aqueous peroxide has been added to the slurry of organic materials. In one embodiment of the invention, the temperature of the raw material feedstock and its reactants are raised by twenty degrees Celsius.

Another embodiment of the invention contemplates adding a mixture of gas comprising oxygen to the dilute, aqueous peroxide, heating the resultant mixture, and then adding the resultant mixture to the first product.

Another embodiment of the invention contemplates:
a) providing an amount of organic materials;
b) forming a slurry from the amount of organic materials;
c) mixing the amount of organic materials with an amount of aqueous peroxide solution; wherein a product is formed;
d) combining the product with a solution, wherein a pretreated substance is formed;
e) removing a substantial portion of the peroxide contained in the pretreated substance; and,
f) incubating the pretreated substance in a reactor for an amount of time sufficient to convert a portion of the product into an amount of methane.

One embodiment of the invention contemplates performing the above steps followed by the additional steps of adding a mixture of gas comprising oxygen to the dilute, aqueous peroxide solution. The mixture of gas could be added to the peroxide solution before the peroxide solution has been contacted with the organic materials. Alternatively, the mixture of the gas could be added contemporaneously with the step of contacting the peroxide solution with the organic materials. An additional alternative would be to first mix the peroxide solution with the organic materials and then bubble in or mix in a mixture of gas.

Alternatively, the process listed above with steps a) through f) contemplates the removal of the peroxide by one or more of the following methods performed in any possible sequence: decanting of the solution after the oxidizing solution has been mixed with the feedstock, filtering the feedstock with a standard filter, chemical methods, photolysis, irradiation, and combinations thereof.

Thus, removal or destruction of peroxide after it has reacted with the organic materials is an important step to the invention. The invention contemplates using various methods to remove or destroy the peroxide. Nonlimiting examples include: washing away the peroxide, chemical removal of peroxide using a catalyst, chemical removal of peroxide using a reducing agent, chemical removal of peroxide using an oxidizing agent, converting the peroxide to a different chemical by using photolysis, adding heat, or different combinations of the above listed techniques. Different combinations of the above listed techniques includes applying two or more of the techniques simultaneously; alternatively, these techniques can be used in various sequences and in combination with additional techniques that are known to one skilled in the art. Photolysis is believed to have certain advantages over the use of caustic acid and bases because caustic acids and bases are relatively expensive and produce waste products that cannot be easily disposed.

Photolytic Removal of Peroxide

Photolysis is defined herein as the splitting of molecules by the absorption of light energy. Ultraviolet light ("UV light") can be used for photolysis of peroxide since hydrogen peroxide, but not water, absorbs light that is in the range of 190 nm to 350 nm. It has been shown that UV light between the wavelengths of 189 nm and 249 nm is ideal for breaking the oxygen-to-oxygen bond in peroxide. Ultraviolet light at these wavelengths does not significantly disrupt the oxygen bonds found in water molecules.

Hydrogen peroxide combined with UV light will form two free hydroxyl radicals (OH), which are potent oxidizing agents. Thus, hydrogen peroxide+UV light=2 OH. The OH radicals that are formed help break down the cellulosic and lignocellulosic materials. Free hydroxyl radicals are believed to attack cellulosic and lignocellulosic materials and help in the degradation of cellulosic and lignocellulosic materials.

The photolysis of $H_2O_2$ by wavelengths of light between 189-249 nm has been shown to split hydrogen peroxide to produce two hydroxyl radicals. These hydroxyl radicals are reactive oxidizing agents. Therefore, the photolysis of peroxide in the presence of organic material enhances the reactivity of the peroxide as well as effectively destroying peroxide.

Ultraviolet radiation is usually divided into four ultraviolet wavelength bands or ranges, a first one of which is the wavelength range of 100-200 nm, a second one of which is the wavelength range of 200-280 nm (conventionally designated UVC), a third one of which is the wavelength range of 280-320 nm (conventionally designated UVB), and a fourth one of which is the wavelength range of 320-400 nm (conventionally designated UVA).

The parameters of the UV-light source and mixing of the reaction mixture can be adjusted so that UV-light penetrates throughout the mixture. One skilled in the art would recognize that there is a tradeoff between the transparency of the slurry and how deeply the light can penetrate through the slurry.

In another embodiment of the invention, the exposure to UV light occurs after the slurry has been removed from the reactor in which peroxide was added. In one nonlimiting embodiment of the invention, the slurry is moved from the initial reactor through a tube or set of tubes and into the digester; alternatively, the UV light could be immersed in the slurry. The tube or set of tubes can be transparent, or they can be partially-transparent. The tube or tubes could have a series of windows that are transparent to UV light. The window could be one large window; alternatively, the windows could be a series of windows that are arranged in a ring around the tube or in a streak that runs along the longitudinal side of the tube. The tube could be configured and could be aligned with UV light sources so that the entire tube is exposed to light.

It is also believed that some of the various methods for processing the slurry with ultraviolet light include batch processing and continuous processing. In batch processing, the entire amount of the slurry that has reacted with the peroxide is then exposed to an UV light source. In continuous processing, a portion of the slurry is exposed to a UV light source. Alternatively, an UV light source could be passed through the slurry itself or around the container that holds the UV light source equipment.

In one embodiment, spectroscopy is used to measure the amount of peroxide that is absorbing the UV light. If the slurry has completed the UV light treatment and still has an amount of peroxide that is not negligible or near zero. In another embodiment at least one sensor device is able to determine the concentration of the slurry and the distance that UV light at a certain parameter will travel through the slurry. In one embodiment an automated system is set-up so that the intensity and duration of the UV light source are varied.

In one embodiment, the slurry is heated either in the initial reactor or in the tubes from which it is transported to the digester. The purpose of the heat is to increase the reactivity of hydrogen peroxide or to break down the hydrogen peroxide.

Alternatively, the UV lights could be moved along the pipe. In another embodiment, the slurry is passed across a catalyst like iron or manganese. The iron acts as a catalyst and, unlike a reactant, a catalyst is not consumed in the reaction. It is believed that the slurry could be passed across a slab of iron or other catalyst. In another embodiment, the catalyst is a porous bed of iron or other metal and the slurry is passed over and through the catalyst. In another embodiment, the catalyst actually lies at the bottom of the tube. In another embodiment, the slab of iron or other catalyst is placed in the initial reactor with the slurry. In another embodiment, the catalyst is placed in the tube that transports material from the initial bioreactor and the slurry is moved across the surface of the catalyst. In another embodiment, the UV light treatment occurs before the catalyst treatment. In another embodiment, the UV light treatment occurs simultaneously with the catalyst treatment. In another embodiment, the UV light treatment occurs after the catalyst treatment.

Alternatively a pulsating beam of ultraviolet is used in one embodiment.

In another embodiment optical fibers are used to disperse the UV light to the slurry. The optical fibers could be placed within the slurry of itself or could be placed surrounding the tube. In one embodiment, two or more different spectra of UV light are used.

In one embodiment, a tube with a window that allows UV light to pass is used, that is, the UV-transparent windows are constructed of a material that will permit UV penetration through the material itself. In one embodiment, the tube may comprise both opaque portions and portions (such as strips) that permit UV penetration into the mixture. It is important that the slurry is mixed so that all parts are exposed to the UV radiation; hence, various means may be used. Mechanical means, electrical means, sonication and other means can be used to transport the slurry through the tube. Mechanical agitation includes mixing via motion generated by a mechanical device.

In one embodiment, the slurry may be heated or cooled to control the rate of reaction. A heat source such as a light may be used to increase the temperature of the slurry, which could increase the rate of the reaction. The contents of US 2008/0045771 are incorporated by reference.

In one embodiment, one or more UV light sources are provided. In some embodiments, a UV light source is used that produces UVA light. In another embodiment a UV light source is used that produces UVB light. In another embodiment a UV light source is used that produces UVC light. In another embodiment, various combinations of UVA, UVB, UVC light, and at various intensities, are used. In one embodiment, the UV light that is used to illuminate the tube is located in direct contact with the tube; in other embodiments the UV light source is located almost touching the tube. In one embodiment the UV light source is partially or fully contained within UV light source housing. In one embodiment a servo-controlled mechanical shutter controls the irradiation by limiting the UV exposure. A UV indicator light may optionally be included to indicate whether the UV lights are on or off. A timer may be used to control the amount of irradiation. In some embodiments it may be desirous to irradiate the mixture at different wavelengths at different times. This may be accomplished by including a sensor system coupled to a computer server that allows for automatic changing of the UV light.

For example, an automated system may be pre-set so that irradiation is provided for 20 minutes at 200 nm, 30 minutes at 240 nm, and 10 minutes at 270 nm. The system may also be set up to deliver UVA, UVB, and UVC light simultaneously or in sequence.

In some embodiments a temperature sensor can be provided to communicate temperature of the UV source to a central processing unit. In one embodiment, the UV source may be sensitive to temperature. For example, as the temperature rises above 90 degrees F., there may be a shift from UVC light to UVB light. Thus, in one embodiment, the temperature sensor can be used to communicate a temperature measurement of the UV light bulb to the central processing unit so that the central processing unit can modify the length of the wavelength.

In one embodiment a processor links the peroxide sensor, and data from the peroxide sensor is combined with an algorithm using the current level from the peroxide sensor and the previous level of the slurry in the tube allows one skilled in the art to determine whether the flow rate of the slurry should be speeded up or slowed down.

In one embodiment the central processing unit is connected to a screen, and the screen displays the sequence of events as they occur in real-time.

One embodiment includes a fluid exit port. The exit point is located so that a minimal sample of effluent can be used to provide a measurable test quantity to assay, if necessary. The embodiments of the invention for photolysis that have been described so far all contemplate transporting the slurry from the initial reactor through a tube or tubes and to the digester, and exposing the slurry to UV light while it is in the tube or tubes. However, other embodiments of the invention contemplate exposing the slurry to the UV light while it is in the initial reactor and before the slurry has entered a tube that leads to the digester. Alternatively, another embodiment of the invention contemplates exposing the slurry while it is in the initial reactor to UV light, and then exposing the slurry to UV light while it is transported in a tube or tubes to the digester.

Thus, in some embodiments of the invention, the peroxide is added to a slurry of organic mass in a reactor and ultraviolet light rays are emitted directly into the reactor after the peroxide has had sufficient time to react with the cellulosic material and lignocellulosic material that may be in the organic mass. Alternatively, in another embodiment of the invention, a transparent tube or optical fiber is passed through the reactor and is surrounded by the slurry of organic material. The tube or optical tube that goes through the core of the reactor is an area where a light source can then be placed which then emits UV light to the organic material. Alternatively, a plurality of tubes or a plurality of optical fibers could travel through the reactor so that UV light could then irradiate internally from the initial reactor, where the organic material is combined with hydrogen peroxide, and collide with hydrogen peroxide molecules that are present in the reactor. In other words, the photolysis occurs in the same reactor in which the hydrogen peroxide interacts with the slurry of organic mass.

In another embodiment of the invention, devices that can emit ultraviolet light are actually passed through the slurry. Some examples of devices include chip, robots, microchips, and nanoparticles that contain ultraviolet sources such as an LED light. In another embodiment of the invention, organic molecules that can emit ultraviolet light are passed through the slurry or a transparent tube that enters the slurry. In another embodiment of the invention, living organisms that can emit ultraviolet light are passed through the slurry or a transparent tube that enters the slurry. It is believed that the use of mirrors may be helpful in distributing the ultraviolet rays throughout the slurry and in managing the ultraviolet light rays that pass through the tube. In many embodiments of the invention, stirring mechanisms are provided to stir and/or agitate the slurry. Some nonlimiting examples of stirrers are: mechanical stirrers, mechanical stirrers with paddles, and magnetic stir bars. All embodiments given herein are given by way of example only and are not limiting.

BRIEF DESCRIPTION OF THE FIGURES

FIG. 3 is a table showing the relationship between the heat that is generated by anaerobic digestion when different volumes of 30% hydrogen peroxide are used to pretreat cellulose.

DETAILED DESCRIPTION OF THE INVENTION

Figure 1A:
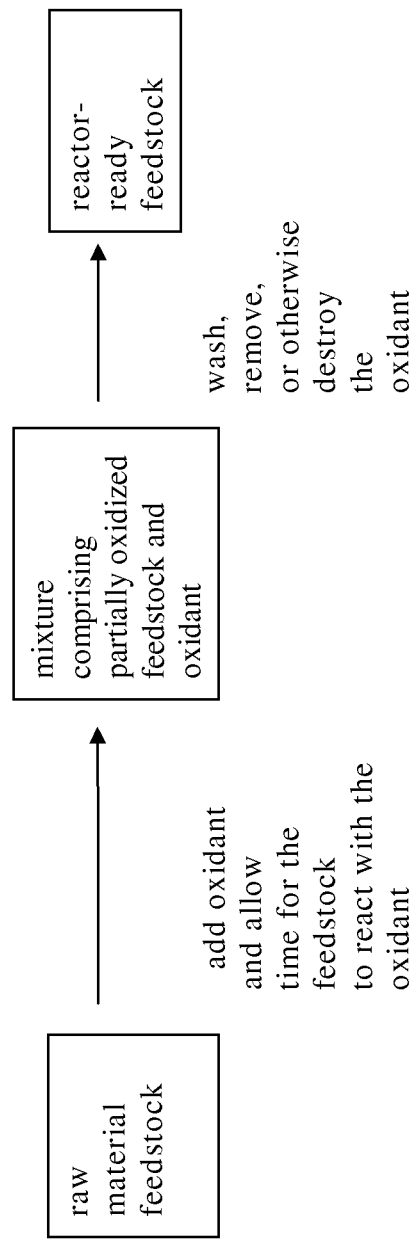
FIG. 1A is a schematic of methods wherein raw material feedstock is exposed to at least one oxidant during pretreatment and then becomes reactor-ready feedstock.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose, and are understood to represent methods and materials generally known to those skilled in the art.

The practice of the present invention will employ, unless otherwise indicated, conventional techniques of biochemistry, chemistry, botany, and biology, which are within the skill of the art. The foregoing techniques and procedures are generally performed according to conventional methods well known to one skilled in the art and as described in various general and more specific references that are cited and discussed throughout the present specification. See for example, *Kirk-Othmer Encyclopedia of Chemical Technology*, $5^{th}$ edition, Raymond Eller Kirk, Jacqueline I. Kroschwitz, Donald Frederick Othmer, Arza Seidel, Wiley-Interscience (2005); *Organic Synthetic Methods*, James R. Hanson, Wiley (2003); and Quantitative Chemical Analysis. $8^{th}$ edition, Daniel C. Harris, WH Freeman and Company (2010), the contents of all of which are incorporated herein by reference. Standard techniques are used for chemical syntheses and chemical analyses, unless described differently herein. The nomenclatures utilized in connection with, and the laboratory procedures and techniques of biochemistry, analytical chemistry, synthetic organic chemistry, atmospheric chemistry, that are described herein are those well known and commonly used in the art.

As utilized with the present disclosure, the following terms, unless otherwise indicated, shall be understood to have the following meanings:

Definitions

As used herein, the term "anaerobic digester" refers to a reactor in which a pretreated substance can be placed and anaerobic organisms are allowed to convert the pretreated substance into bioenergy. As used herein, the term "partially-anaerobic digester" is similar to an anaerobic digester; however, the reactor may be specifically designed to accommodate mixed cultures of aerobic and anaerobic organisms. The anaerobic and aerobic organisms can include, but are not limited to archaea, bacteria, yeast, fungi, plant cells, animal cells and genetically-engineered organisms which are selected for their ability to bioconvert the substrate and produce a selected product. Non-limiting examples of anaerobic and partially-anaerobic digesters include: anaerobic activated sludge process, anaerobic clarigester, anaerobic contact process, anaerobic expanded-bed reactor, anaerobic filter, anaerobic fluidized bed, anaerobic lagoon, anaerobic migrating blanket reactor, batch system anaerobic digester, continuous stirred-tank reactor (CSTR), expanded granular sludge bed digestion (EGSB), hybrid reactor, Imhoff tank, induced blanket reactor, internal circulation reactor (IC), one-stage anaerobic digester, partial mixing anaerobic digester, submerged media anaerobic reactor, two-stage anaerobic digester, upflow anaerobic sludge blanket digestion (UASB), upflow and down-flow anaerobic attached growth, etc.

As used herein "aqueous" means: "made from, with, or by water." *Merriam-Webster's Medical Dictionary*, available at www.merriam-webster.com.

As used herein, the term "bioenergy" refers to "useful, renewable energy directly or indirectly produced from organic matter." Non-limiting examples include biogas (also known as swamp gas, sewer gas, and fuel gas), biomass, biofuel, power alcohol and gasifiers. Bioenergy can yield liquids, solids, gaseous fuels, electricity, heat, chemicals, and other materials." (Definitions for bioenergy derived from en.wikipedia.org, www.biorenew.iastate.edu, and www.offsetopportunity.com.) Biogas is typically 50-75% methane, 25-50% carbon dioxide, and may contain sulfides, water vapor, and ammonia. See N. Stalin and H. J. Prabhu, "Performance Evaluation of Partial Mixing Anaerobic Digester", *ARPN Journal of Engineering and Applied Sciences*, Vol. 2 No. 3, 2007.

As used herein, the term "catalysts" refers to a chemical substance that can participate in a reaction and indirectly or directly speed up a reaction or slow down a reaction: includes heterogeneous catalysts, homogeneous catalysts, organocatalysts, enzymes, and biocatalysts. Non-limiting examples include palladium, proton acids, multifunctional solids (such as alumina), transition metals, platinum metals, and precatalysts (such as Wilkinson's catalyst). Examples of catalysts that indirectly speed up or slow down reactions are promoters and catalytic poisons.

As used herein "the concentration of the peroxide is a sufficiently low enough concentration of peroxide to avoid excess foaming" means that the concentration of the peroxide is of such an amount that the volume of any foam that occurs during the reaction is no greater than three times the volume of the reactor.

As used herein "dilute" means: "of relatively low strength or concentration." *Merriam-Webster's Medical Dictionary*, available at www.merriam-webster.com.

As used herein, "hemicelluloses" refers to "any of various plant polysaccharides less complex than cellulose and easily hydrolysable to monosaccharides and other products." *Merriam-Webster's Medical Dictionary*, available at http://www.merriam-webster.com.

As used herein, "irradiation" refers to the exposure of an object to radiation.

The term "lignocellulose-containing material" or "lignocellulosic material" means any type of organic material comprising cellulose, hemicellulose, lignin, or combinations thereof. Non-limiting examples include: algae, woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, sugar-processing residues, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; and forestry wastes, such as but not limited to recycled wood pulp fiber, sawdust, hardwood (e.g., poplar, oak, maple, birch), softwood, or any combination thereof. Lignocellulosic material may comprise one species of fiber; alternatively, lignocellulosic material may comprise a mixture of fibers that originate from different lignocellulosic materials. Particularly advantageous lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and *miscanthus*; or combinations thereof.

As used herein, the term "organic material" refers to a carbohydrate-containing material and can also refer to a polysaccharide-containing material. It can also refer to a cellulose-, hemicellulose-, or lignocellulose-containing material. Organic material is commonly obtained from but is not limited to the following examples: wood, plants, residue from agriculture or forestry, organic component of municipal and industrial wastes, primary sludges from paper manufacture, waste paper, waste wood (e.g., sawdust), wood, wood chips, rice straw, rice hulls, bagasse, corn stalks and corn cobs; newspaper, corrugated cardboard, waste paper, pulp waste and cellulosic materials contained in municipal and industrial wastes, agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphtha, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above. The aforementioned examples are merely illustrative and not limiting.

As used herein, the term "oxidizing agent" or "oxidant" means an element or compound that can participate in a reduction-oxidation reaction and gains electrons in a reduction-oxidation reaction. Oxidizing agents oxidize other species and are themselves reduced. Non-limiting examples include: oxygen, ozone, fluorine, chlorine, bromine, iodine, hypochlorite, chlorate, nitric acid, chromium trioxide, chromate, dichromate, permanganate, manganate, persulfate, permanganate, chromate, chlorate, chlorite, hypochlorite and peroxides.

As used herein, the term "oxidant solution" means a solution containing an oxidant.

As used herein, the term "peroxide" means any molecule or compound that contains an oxygen-oxygen single bond, that is, (R—O—O—R'). A typical example is hydrogen peroxide. Other non-limiting examples include sodium peroxide, superoxides, ozones, ozonides, and hydroperoxides.

As used herein, the term "reactor" means any vessel, such as a digester, that is suitable for practicing a method of the present invention and is synonymous with "bioreactor."

As used herein, the term "reducing agent" or "reductant" means an element or compound that can participate in a reduction-oxidation reaction and loses electrons in a reduction-oxidation reaction. Reducing agents reduce other species and are themselves oxidized. Non-limiting examples include: lithium, lithium aluminum hydride, hydrazine, sodium, sodium amalgam, magnesium, sodium borohydride, aluminum, nascent hydrogen, chromium, ferrous iron, stannous iron, iron, tin, copper, silver, sulfite compounds, bromine, chloride, zinc-mercury amalgam, diisobutylaluminum hydride (DIBAH), a Lindlar catalyst, oxalic acid, formic acid, carbon, and hydrocarbons.

As used herein, the term "removing" means to physically take away objects from a reaction so that the objects no longer participate in the reaction or to chemically deactivate a reactant or to react with the object or to catalyze a reaction that effectively removed the object. Some other non-limiting examples of removing an object or objects are to drain away the objects or to decant the object or objects. Another common method of removing objects is to decant a solution or suspension and then filter the remaining precipitate. One example is the addition of a catalyst to a peroxide solution to convert the peroxide to water and oxygen. Another example of removing a peroxide is the photolysis of a solution containing peroxide, which results in the inactivation of the peroxide.

As used herein, the term "sufficiently partially oxidize the raw material feedstock" means to oxidize a sufficient number of the bonds in the cellulosic or lignocellulosic materials contained in the raw material feedstock such that the resultant reactor-ready feedstock can be incubated and generate methane.

As used herein, the term "slurry" refers to: a watery mixture of insoluble material. *Merriam-Webster's Dictionary*, available at www.merriam-webster.com. The following method for creating a slurry is only one of the many possible methods for creating a slurry: collecting waste materials from various sources; pre-separating the waste materials into organic and inorganic materials; reducing the size of the waste materials by shredding or grinding; adding water; and, creating a suspension of organic waste materials or creating a true solution of waste materials.

As used herein, the phrase "washing the first product with a solution comprising oxygen" means: adding a mixture of gas comprising oxygen to the dilute, aqueous peroxide solution and then contemporaneously mixing the dilute, aqueous peroxide solution with the slurry of organic materials; or, it could also mean: first, mixing the dilute, aqueous peroxide solution with the slurry of organic materials, followed by adding a mixture of gas to the mixture of dilute, aqueous peroxide solution and the slurry of organic materials. The mixture of gas may contain oxygen alone, or it may contain oxygen in combination with other gases. One purpose of adding oxygen gas is to increase the oxidation of the organic materials. Optionally, the mixture of gas could be bubbled into the dilute, aqueous peroxide solution.

METHODS AND EXAMPLES

Background for Method

Figure 1B:
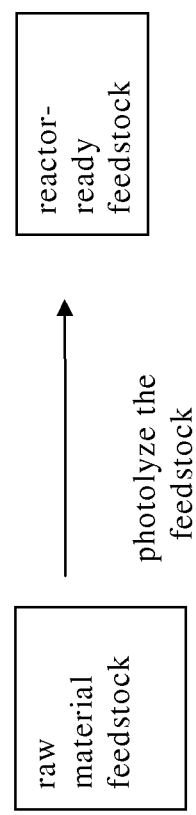
FIG. 1B is a schematic of methods wherein raw material feedstock is photolyzed during pretreatment and then becomes reactor-ready feedstock.
Figure 1C:
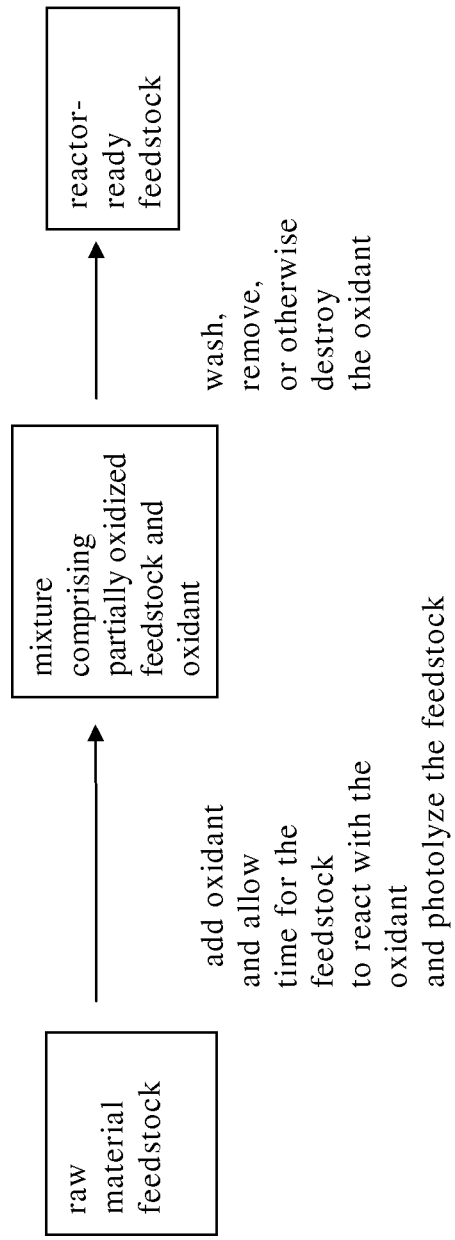
FIG. 1C is a schematic of methods wherein raw material feedstock is photolyzed during pretreatment and exposed to at least one oxidant during pretreatment and then becomes reactor-ready feedstock.

Although there are many methods and processes known in the art for conversion of organic materials, these methods and processes generally cannot effectively breakdown cellulose and lignocelluloses into forms that can be readily converted into bioenergy. Referring to FIG. 1, this invention relates to processes for improving the efficiency of converting organic materials into: bioenergy, products that can be converted into bioenergy, or waste materials with less mass and volume. Specifically, the methods begin with raw material feedstock such as human sewage, grass clippings, etc. The methods then disclose a pretreatment phase wherein an oxidizing agent, such as peroxide or peroxide and oxygen, is added to raw material feedstock. The oxidizing agent is allowed to react with the raw material feedstock; UV radiation may also be used to treat the feedstock before, during, or after a reaction with the oxidizing agent has occurred. The oxidizing agent disrupts the bonds of cellulosic and lignocellulosic material contained in the raw material feedstock and results in the formation of a mixture comprising partially oxidized feedstock and peroxide (or other oxidizing agent). The final step is to remove peroxide (or other oxidizing agent) that remains in the mixture comprising partially oxidized feedstock and peroxide. The peroxide (or other oxidizing agent) can be removed by: washing, decanting, physically removing the peroxide (or other oxidizing agent), chemically-inactivating the peroxide (or other oxidizing agent), photolyzing the peroxide (or other oxidizing agent), or any other method that effectively destroys the peroxide (or other oxidizing agent). The step of removing the peroxide (or other oxidizing agent) converts the mixture comprising partially oxidized feedstock and peroxide (or other oxidizing agent) into reactor-ready feedstock. Because the chemical bonds of the cellulosic and lignocellulosic materials have been disrupted, the reactor-ready feedstock can be economically converted to bioenergy, products that can be used to form bioenergy, or waste materials with less volume and mass, and because the peroxide (or other oxidizing agent) has been removed from the mixture comprising partially oxidized feedstock and peroxide (or other oxidizing agent), the reactor-ready feedstock will not excessively foam when it is incubated in a reactor.

One advantage of the invention over the ozone process disclosed in U.S. Pat. No. 6,835,560 is that dilute, aqueous peroxide is used, which is less expensive than ozone, easier to use, and simpler. In addition, the '560 patent discloses a process that uses acids, which is more expensive and also has negative effects on digester operation.

The methods of the present invention contemplate using a peroxide solution to disrupt the long-chain polymer linkages of organic materials. The disruption of long-chain polymer linkages increases the susceptibility of the polymer chains to further breakdown by bacteria and archaea. The reactor-ready feedstock, that is, the pretreated organic material, can then be used as a substrate stream for an anaerobic induced blanket reactor ("IBR") or other type of reactor comprised of organisms such as bacteria or archaea. Certain types of the organisms can then digest the pretreated cellulosic and lignocellulosic materials and, consequently, convert the pretreated organic materials into products, such as methane and compost.

Removal of the peroxide is an important aspect of the invention. Some non-limiting examples of methods for removal of peroxide include: draining away the peroxide, decanting the peroxide, filtering the organic materials after they have been contacted with peroxide, and chemical- or photolytic-inactivation of the peroxide. Other examples include: decanting a solution or suspension that contains peroxide and then filtering the remaining precipitate; and, adding a catalyst to a peroxide-containing solution to convert the peroxide to water and oxygen.

Methods and Results for Examples

The following methods are illustrative of one of many methods that could be used to practice the invention.

FIG. 2

Figure 2:
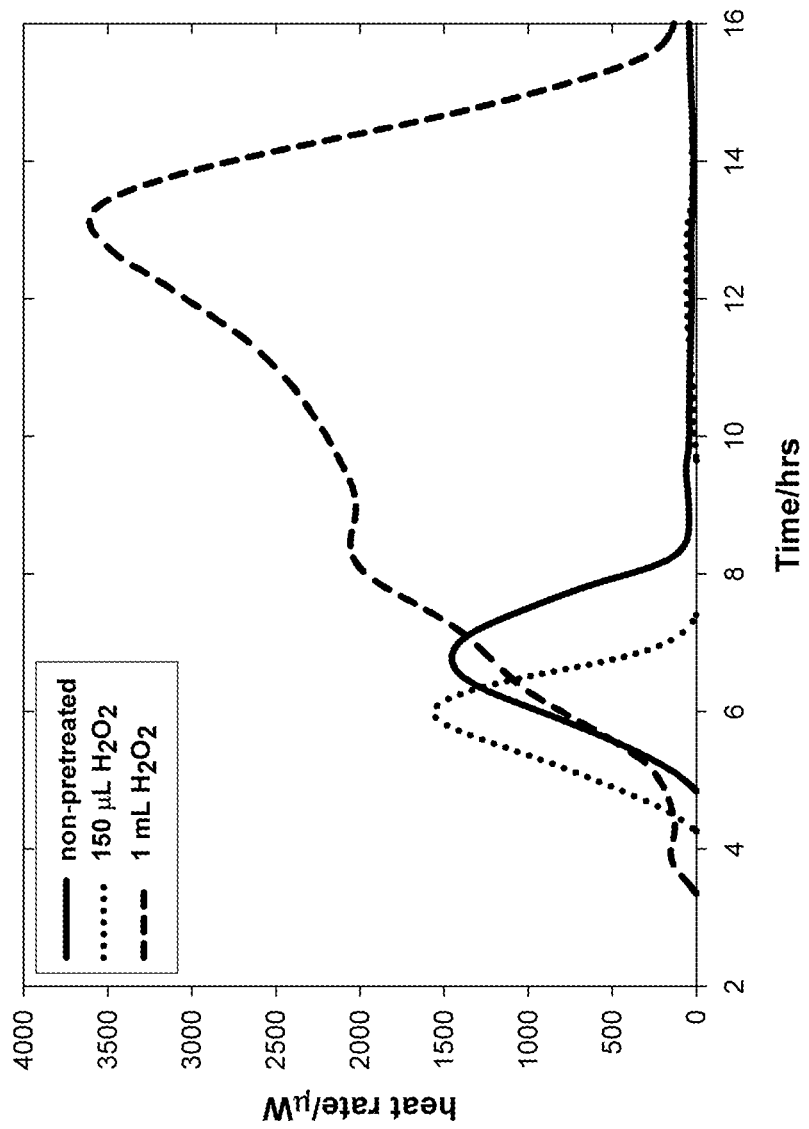
FIG. 2 is a plot of the heat liberated from the reaction of untreated cellulose and pretreated cellulose with a mixed culture of anaerobic bacteria.

In an effort to quantify the enhancement in cellulose breakdown due to the pretreatment with peroxide, an isothermal heat-conduction calorimeter with 3 sample and 1 reference cell (model IMC from calorimetry Sciences Corp., Lindon, Utah) was used to monitor the rate of heat liberated from samples pretreated with increasing amounts of peroxide. Plotted in FIG. 2 is the heat liberated from 3 samples containing the same amount of cellulose but with varying amounts of pretreatment by peroxide.

The dashed curve represents the heat liberated from a cellulose sample that had no pretreatment by hydrogen peroxide. Sludge (10 mL) from an operating anaerobic digester was added to untreated cellulose and allowed to react. The dashed-dot curve was pretreated by adding 150 µL of 30% hydrogen peroxide and allowing it to react for approximately 12 hours.

The sample was then washed with distilled water and filtered. 10 mL of active sludge (mixed culture) obtained from a working anaerobic digester was added to this sample. The solid curve shows the heat liberated from a cellulose sample that was pretreated with 1 mL of 30% hydrogen peroxide and then allowed to react for approximately 12 hours. The sample was then washed with distilled water and filtered. After drying, 10 mL of active sludge was added to this sample. Examination of FIG. 1 shows that the most heat was liberated from the sample (solid curve) in which 1 mL of 30% hydrogen peroxide was added in the pretreatment step. Some heat is liberated from the reaction of nontreated cellulose with the mixed culture of anaerobic bacteria (dashed curve). This is attributed to the reaction of hemicellulose with the mixed culture. (Hemicellulose is naturally occurring). This is consistent with previous research showing that upwards of 30% of a cellulose sample (by mass) introduced into an IBR can be digested. The solid curve shows that approximately 7.2 times more heat is liberated, compared to the untreated cellulose sample (dashed curve), if the cellulose has been pretreated with 1 mL of 30% hydrogen peroxide. Shown in FIG. 3 is a table of the ratio of heat liberated from pretreated cellulose/untreated cellulose versus increasing the volume of hydrogen peroxide used to pretreat the sample. The relationship observed between the amount of heat produced and the amount of peroxide used to treat the cellulose suggests that the efficiency of breakdown of the cellulose into smaller digestible pieces due to pretreatment with hydrogen peroxide is correlated with the molar ratio of cellulose to peroxide.

FIG. 3

A suspension of cellulosic and lignocellulosic materials was formed by stirring finely divided lignocellulose into an aqueous solution of peroxide. The concentration of the peroxide used was not as critical as the molar ratio of cellulose/peroxide. The molar ratio of cellulose was determined empirically from the data shown in FIG. 3. (For a scaled-up version of the method, the molar ratio could be estimated based on the molecular weight of cellulose and the actual or estimated weight of the cellulosic and lignocellulosic materials.) The molecular weight of cellulose monomer is approximately 360 gm/mole. FIG. 3 shows that ratios of peroxide/cellulose that approach 1 mole of hydrogen peroxide to 360 g of cellulose optimize the conversion of the pretreated cellulose and lignin into methane in a bioreactor. The reaction was allowed to react at room temperature after which peroxide was removed from the solution by decanting and the products were then introduced into a reactor. The inventors theorize, but are not limited to the following theory, that the net effect of pretreatment was to disrupt the long-chain polymer linkage backbone in cellulose and lignin and consequently leave smaller polymer chains that are more readily digested by a mixed culture of bacteria and archaea found in many bioreactors. It is expected that mixed cultures of aerobic bacteria would also be capable of digesting this substrate as well.

FIG. 4

Figure 4:
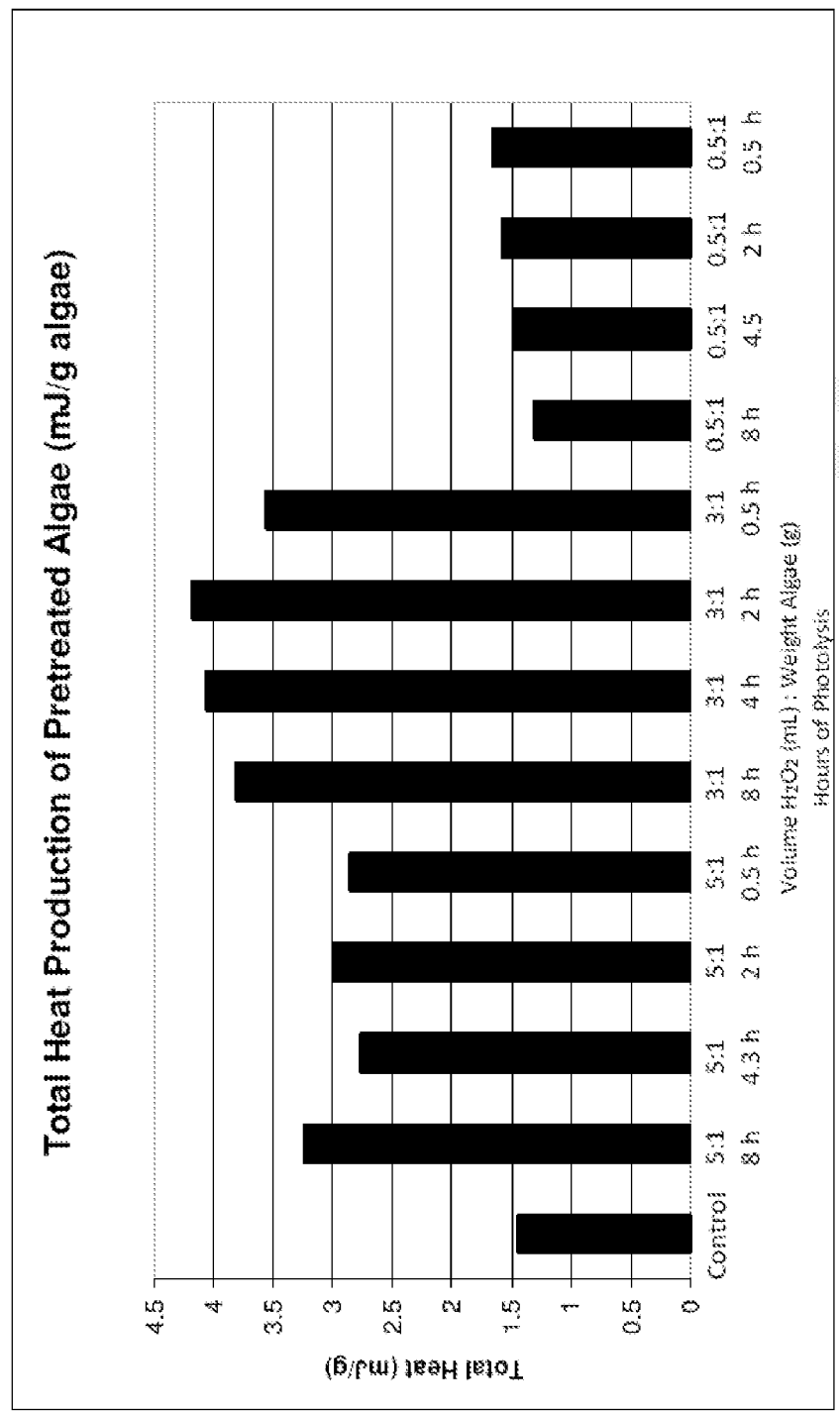
FIG. 4 is a bar chart showing the effect of decreasing hydrogen peroxide concentration and photolysis time on the total heat liberated from a sample of algae.

The total heat calculated by integration of the thermograms, which is proportional to the overall conversion efficiency for gas production without regard to residence time, is depicted in FIG. 4. FIG. 4 shows the effect of decreasing hydrogen peroxide concentration and photolysis time on the total heat liberated from a sample of algae. Samples of algae were pretreated with various ratios of hydrogen peroxide to algae followed by photolysis with UV light at various periods of time. The most metabolic heat, and therefore the most gas, is liberated from samples treated with 3 mL of peroxide. Treatment with 5 mL of peroxide produced less heat, and treatment with 0.5 mL peroxide is not significantly different from the control. The control was algae suspended in water; and the control that was not treated with peroxide and was not exposed to UV light. No significant increase in heat production occurred from irradiation times longer than 0.5 h, indicating this is sufficient to destroy enough peroxide to prevent excess foaming and destruction of the culture. FIG. 2 shows the total heat produced as calculated from integration of the recorded thermogram and normalized to the algae dry weight. Error bars are shown for the averages of samples that were run in duplicate. Bars are labeled according to the ratio of mL of 30% $H_2O_2$ to grams of algae (wet weight) and hours of irradiation.

The results and examples are given as illustrations; it should be noted that in different situations using different substrates and/or different concentrations of substrates, the parameters may need to be adjusted. The examples and principles presented herein should be sufficient for one skilled in the art to determine those principles without undue experimentation. It should be appreciated that the processes and methods of the present invention are capable of being incorporated in the form of a variety of embodiments, only a few of which have been illustrated and described above. The invention may be embodied in other forms without departing from its spirit or essential characteristics. For example, the effectiveness of peroxide treatment may be enhanced with photolysis with UV radiation or UV radiation alone may be used as the pretreatment. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

The invention claimed is:

1. A process for treating organic materials in order to minimize the cost-benefit ratio of converting the organic material to biofuel; the process comprises the steps of
    a. providing an aqueous slurry comprising organic materials;
    b. contacting said aqueous slurry with a solution comprising an amount of peroxide;
    c. forming a mixture comprising said aqueous slurry and said solution, wherein the concentration of peroxide in said mixture is at least 1 ppm, said amount of peroxide being sufficient to oxidize at least a portion of said organic materials into an oxidized product and wherein said oxidized product comprises an amount of organic peroxide;
    d. photolyzing at least a portion of said amount of said organic peroxide, thereby deactivating at least 5% of said amount of said organic peroxide wherein said photolyzing is accomplished by exposing said organic peroxide to wavelengths of an electromagnetic light in the range between 189 nm to 350 nm inclusive; and wherein said oxidized product produces at least 50% less foam than said oxidized product would have without photolyzing said at least a portion of said amount of said organic peroxide; and
    e. adding bacteria to said oxidized product.

2. The process of claim 1, further comprising the steps of
    a. contacting said oxidized product with at least one microorganism in a reactor;
    b. converting said oxidized product into a metabolic product, said metabolic product comprising a hydrocarbon gas; and
    c. collecting said metabolic product.

3. The process of claim 1, further comprising the steps of
a. contacting said oxidized product with at least one microorganism;
b. converting said oxidized product into a metabolic product, said metabolic product comprising hydrogen gas; and
c. collecting said metabolic product.

4. The process of claim 2, wherein said hydrocarbon gas is at least one of the following selected from the group consisting of methane and hydrogen.

5. The process of claim 2, wherein said at least one microorganism comprises a methanogenic bacteria and wherein said hydrocarbon gas comprises methane.

6. The process of claim 1, further comprising the steps of
a. photolyzing at least a portion of said amount of peroxide for a first period of time;
b. photolyzing said organic materials for said first period of time, wherein the steps of photolyzing said at least a portion of said amount of peroxide and photolyzing said organic materials accelerates the rate at which said organic material is converted into oxidized product;
c. photolyzing at least a portion of said amount of peroxide for a second period of time; and
d. photolyzing at least a portion of said organic materials, wherein the steps of 1) photolyzing said at least a portion of said amount of peroxide and 2) photolyzing at least a portion of said organic materials decelerates the rate at which organic material is converted into oxidized product.

7. The process of claim 1, wherein said oxidized product is washed with at least one washing agent, wherein said at least one washing agent is selected from the group consisting of water, distilled water, deionized-distilled water, polar substances, catalysts, oxidizing agents, reducing agents, and combinations thereof.

8. The process of claim 1, wherein a ratio of moles of said peroxide to moles of said organic materials is at least greater than 1 mole of peroxide to 100 moles of organic material.

9. The process of claim 1, wherein said organic material comprises lignocellulosic material and the ratio of moles of peroxide to moles of lignocellulosic material in said organic material is greater than 1 mole of peroxide to 100 moles of lignocellulosic material.

10. The process of claim 9, wherein the step of photolyzing at least a portion of said amount of organic peroxide is accomplished by exposing said organic peroxide to wavelengths of electromagnetic light, wherein said wavelengths are greater than 189 nm and less than 401 nm.

11. The process of claim 9, wherein said organic materials comprises at least one of the following: materials selected from the group consisting of food industry waste, animal waste, paper industry waste, municipal solid waste, tire waste, petroleum refining waste, and biomass.

12. The process of claim 1, wherein said peroxide is selected from the group consisting of hydrogen peroxide, peroxide, sodium percarbonate, sodium peroxycarbonate, sodium peroxide, calcium peroxide, organic peroxides, barium peroxide, superoxides, and any compound capable of producing a peroxide in water.

13. A method of producing methane from organic materials comprising the steps of:
a. providing an amount of organic material;
b. forming a slurry from the amount of organic material;
c. mixing the amount of the organic material with an amount of peroxide solution; wherein said mixing generates a product which comprises an amount of organic peroxide;
d. combining the product with a chemical solution, wherein said combining produces a pretreated substance;
e. photolyzing at least a portion of said amount of organic peroxide, thereby deactivating at least 5% of said amount of organic peroxide, wherein said product produces at least 50% less foam than said product would have without photolyzing said at least a portion of said amount of said organic peroxide; and
f. incubating the pretreated substance in a reactor for a period of time sufficient to convert a portion of the product into an amount of methane.

14. The method of claim 13, wherein the product that has been substantially freed from organic peroxide contains a sufficiently low concentration of said organic peroxide, wherein said product is substantially free from foam when introduced into the reactor, wherein said reactor is selected from the group consisting of anaerobic reactors and partially-anaerobic reactors.

* * * * *